(12) United States Patent
Ma et al.

(10) Patent No.: US 9,908,906 B2
(45) Date of Patent: Mar. 6, 2018

(54) LUMINESCENT METAL HALIDE PEROVSKITES AND METHODS

(71) Applicant: FLORIDA STATE UNIVERSITY RESEARCH FOUNDATION, INC., Tallahassee, FL (US)

(72) Inventors: Biwu Ma, Tallahassee, FL (US); Zhao Yuan, Tallahassee, FL (US)

(73) Assignee: Florida State University Research Foundation, Inc., Tallahassee, FL (US)

( * ) Notice: Subject to any disclaimer, the term of this patent is extended or adjusted under 35 U.S.C. 154(b) by 0 days.

(21) Appl. No.: 15/354,558

(22) Filed: Nov. 17, 2016

(65) Prior Publication Data

US 2017/0166596 A1    Jun. 15, 2017

Related U.S. Application Data

(60) Provisional application No. 62/267,342, filed on Dec. 15, 2015.

(51) Int. Cl.
| | |
|---|---|
| C09K 11/06 | (2006.01) |
| C07F 7/24 | (2006.01) |
| H01L 51/42 | (2006.01) |
| C09K 11/02 | (2006.01) |

(52) U.S. Cl.
CPC ............. *C07F 7/24* (2013.01); *C09K 11/06* (2013.01); *H01L 51/4226* (2013.01); *C09K 2211/188* (2013.01)

(58) Field of Classification Search
CPC ...... C07F 7/24; C09K 11/06; C09K 2211/188
See application file for complete search history.

(56) References Cited

U.S. PATENT DOCUMENTS

| | | | |
|---|---|---|---|
| 5,882,548 A | 3/1999 | Liang et al. | |
| 6,344,662 B1 | 2/2002 | Dimitrakopoulos et al. | |
| 2015/0357591 A1* | 12/2015 | Karunadasa | ........ H01L 51/4226 136/256 |

FOREIGN PATENT DOCUMENTS

WO    2015/061555 A1    4/2015

OTHER PUBLICATIONS

Audebert et al., "Synthesis of New Perovskite Luminescent Nanoparticles in the Visible Range," Chem. Mater., 2009, 21:210-214.

Cao et al., "2D homologous Perovskites as Light-Absorbing Materials for Solar Cell Applications," Journal of the American Chemical Society, 2015, 137:7843-7850.
Dou et al., "Atomically Thin Two-Dimensional Organic-Inorganic Hybrid Perovskites," Science, 2015, 349:6255:1518-1521.
Gonzalez-Carrero et al., "Blue-Luminescent Organic Lead Bromide Perovskites: Highly Dispersible and Photostable Materials," J. Mater. Chem. A, 2015, 3:14039-14045.
Gonzalez-Carrero et al., "Maximizing the Emissive Properties of CH3NH3PbBr3 Perovskite Nanoparticles," J. Mater. Chem. A, 2015, 3:9187-9193.
Zhang et al., "Enhancing the Brightness of Cesium Lead Halide Perovskite Nanocrystal Based Green Light-Emitting Devices through the Interface Engineering with Perfluorinated Ionomer," Advanced Science, 2015, 2:1500194.
Jang et al., "Reversible Halide Exchange Reaction of Organometal Trihalide Perovskite Colloidal Nanocrystals for Full-Range Band Gap Tuning," Nano Lett., 2015, 15:5191-5199.
Kim et al., "Multicolored Organic/Inorganic Hybrid Pervskite Light-Emitting Diodes," Adv. Mater., 2014, pp. 1-7.
Muthu et al., "Structural Transition of ETS1 from an Auto-Inhibited to Functional State Upon Association with the p16INK4a Native and Mutated Promoter Region," RSC Adv., 2016, 1-16.
Noh et al., "Chemical Management for Colorful, Efficient, and Stable Inorganic-Organic Hybrid Nanostructured Solar Cells," Nano Lett., 2013, 13, 1764-1768.
Pellet et al., "Transforming Hybrid Organic Inorganic Perovskites by Rapid Halide Exchange," Chem. Mater., 2015, 27, 2181-2188.
Schmidt et al., "Nontemplate Synthesis of CH3NH3PbBr3 Perovskite Nanoparticles," J. Am. Chem. Soc., 2014, 136:850-853.
Sichert et al., "Quantum Size Effect in Organometal Halide Perovskite Nanoplatelets," Nano. Lett., 2015, 15:6521-6527.
Smith et al., "A Layered Hybrid Perovskite Solar-Cell Absorber with Enhanced Moisture Stability," Angew. Chem. Int. Ed., 2014, 53:1-5.
Vybornyi et al., "Polar-Solvent-Free Colloidal Synthesis of Highly Luminescent Alkylammonium Lead Halide Perovskite Nanocrystals," Nanoscale, 2016, 8:6278-6283.
Zhang et al., "Brightly Luminescent and Color-Tunable Colloidal CH3NH3PbX3 (X = Br, I, Cl) Quantum Dots: Potential Alternatives for Display Technology," Acs. Nano., 2015, 9:4533-4542.
PCT International Search Report and Written Opinion for PCT Application No. PCT/US2016/062520 dated Feb. 24, 2017 (12 pages).
Mitzi et al., "Preparation and Properties of (C4H9NH3)2EuI4: A Luminescent Organic-Inorganic Perovskite with a Divalent Rare-Earth Metal Halide Framework," Chem. Mater, 1997, 9:2990-2995.

* cited by examiner

*Primary Examiner* — Pancham Bakshi
(74) *Attorney, Agent, or Firm* — Eversheds Sutherland (US) LLP

(57) ABSTRACT

Nanoscale metal halide perovskites are provided. The nanoscale metal halide perovskites may have a 2D structure, a quasi-2D structure, or a 3D structure. Methods also are provided for making the nanoscale metal halide perovskites. The color emitted by the nanoscale metal halide perovskites may be tuned.

11 Claims, 4 Drawing Sheets

LUMINESCENT METAL HALIDE PEROVSKITES AND METHODS

CROSS-REFERENCE TO RELATED APPLICATIONS

This application claims priority to U.S. Provisional Patent Application No. 62/267,342, filed Dec. 15, 2015, which is incorporated herein by reference.

BACKGROUND

Earth abundant organometal halide perovskites have emerged as a promising class of light emitting materials that may exhibit high color purity and tunability. While bulk perovskite thin films can be prepared by relatively facile low temperature solution processing, they often suffer from low photoluminescence quantum efficiency (PLQE), possibly due to emission quenching caused by defects. Although single crystalline nano/microscale perovskites have demonstrated high PLQEs, they have been prepared only by wet-chemistry methods. For example, green emitting nanoscale three-dimensional (3D) methylammonium lead bromide perovskites (MAPbBr$_3$) prepared by wet-chemistry techniques have shown PLQEs up to 93%. (see, e.g., L. C. Schmidt et al. *J. Am. Chem. Soc.,* 2014, 136, 850-853; S. Gonzalez-Carrero et al. *J. Mater. Chem. A,* 2015, 3, 9187-9193; H. Huang et al. *Advanced Science,* 2015, 2, 1500194; C. Muthu et al. *Rsc. Adv.,* 2014, 4, 55908-55911; and O. Vybornyi et al. *Nanoscale,* 2016, DOI: 10.1039/c5nr06890h).

Highly luminescent two-dimensional (2D) layered lead bromide perovskite nano/microdisks with deep blue emissions also have been reported (S. Gonzalez-Carrero et al. *J. Mater. Chem. A,* 2015, 3, 14039-14045; P. Audebert et al. *Chem. Mater.,* 2009, 21, 210-214; L. T. Dou et al. *Science,* 2015, 349, 1518-1521). In addition to higher PLQEs, these nanoscale perovskites also have shown purer and narrower emissions, and higher stability, as compared to their bulk counterparts. The methods used to synthesize these perovskites and others, however, typically are difficult, suffer from relatively low product yields, and/or do not produce high quality perovskites either consistently or at all.

Organometal halide perovskites also have been demonstrated to exhibit high color tunability across the visible to near infrared regions. This feature has been explored through synthetic control of 3D perovskite structures by using different halide anions, i.e., Cl, Br, I, and their mixtures (see, e.g., F. Zhang et al. *Acs. Nano.,* 2015, 9, 4533-4542; D. M. Jang et al. *Nano. Lett.,* 2015, 15, 5191-5199; N. Pellet et al. *Chem. Mater.,* 2015, 27, 2181-2188; Y. H. Kim et al. *Adv. Mater.* 2015, 27, 1248-1254; and J. H. Noh et al. *Nano. Lett.* 2013, 13, 1764-1769).

The use of bulk quasi-2D layered lead(II) iodide perovskites with tunable absorptions as light absorber in photovoltaic cells (PVs) has been reported (I. C. Smith et al. *Angew. Chem. Int. Edit.,* 2014, 53, 11232-11235; and D. H. Cao et al. *J. Am. Chem. Soc.,* 2015, 137, 7843-7850). Although these hybrid perovskites have shown better moisture resistance than pure 3D perovskites, the color tuning of perovskites by organic cations remains challenging, due at least in part to the wet-chemistry techniques used to prepare them. This likely is due, at least in part, to the difficulty associated with controlling crystal growth in a solution phase containing different organic cations. Due at least in part to this difficulty, non-uniform products with impure emissions often are produced.

Also, the color tuning of lead (II) bromide perovskites by using organic cations to control the thickness of the obtained nanoplatelets has been reported, but the products suffer from relatively low quantum efficiency, and their emissions are not pure, i.e., include broad and multiple peaks, due at least to the fact that the process results in the formation of mixed perovskites having different thicknesses (J. A. Sichert et al. *Nano. Lett.,* 2015, 15, 6521-6527).

Therefore, there remains a need for nanoscale metal halide perovskites that are stable, color tunable, exhibit narrow emissions, have high quantum efficiencies, and/or are capable of being made by a relatively simple process that may permit control over the crystalline structure of the nanoscale metal halide perovskites.

BRIEF SUMMARY

Provided herein are nanoscale metal halide perovskites. In embodiments, the nanoscale metal halide perovskites comprise a crystal having a unit cell according to formula (I) or (II):

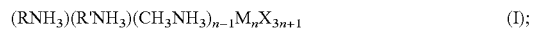
$$(RNH_3)(R'NH_3)(CH_3NH_3)_{n-1}M_nX_{3n+1} \quad (I);$$

$$(RNH_3)(R'NH_3)(IC)_{n-1}M_nX_{3n+1} \quad (II);$$

wherein R and R' independently are a monovalent $C_6$-$C_{20}$ hydrocarbyl; IC is an inorganic cation comprising a monovalent metal; M is a metal selected from Pb, Sn, Cu, Ge, Mn, Co, Bi, or Eu; X is a halide ion selected from Cl, Br, or I; and n is an integer equal to or greater than 1. In one embodiment, the crystal of the nanoscale metal halide perovskite has a 2D structure. In another embodiment, the crystal of the nanoscale metal halide perovskite has a quasi-2D structure. In yet another embodiment, the crystal of the nanoscale metal halide perovskite has a 3D structure.

Also provided herein are methods of forming nanoscale metal halide perovskites. In embodiments, the methods comprise providing a precursor liquid comprising a first polar organic liquid, a metal halide, and at least two cations selected from the group consisting of [1] a small cation, [2] RNH$_3$, and [3] R'NH$_3$, wherein R and R' are selected independently from a $C_6$-$C_{20}$ hydrocarbyl, and the small cation is CH$_3$NH$_3$ or an inorganic cation comprising a monovalent metal; and contacting the precursor liquid with a second polar organic liquid to form the nanoscale metal halide perovskite. In one embodiment, the methods further comprise providing a first liquid comprising a metal halide and the first polar organic liquid; providing a second liquid comprising the at least two cations; and combining the first liquid and the second liquid to form the precursor liquid.

DETAILED DESCRIPTION

Figure 1:
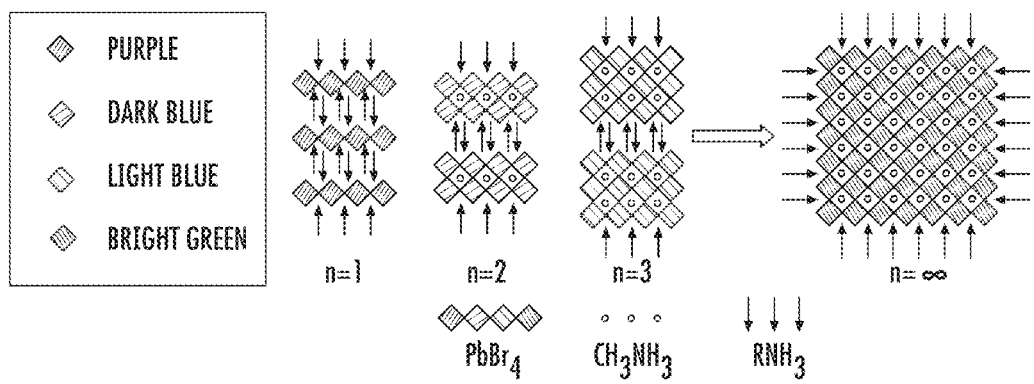
FIG. 1 is a schematic of various crystal structures of several embodiments of nanoscale metal halide perovskites.

Provided herein are nanoscale metal halide perovskites, such as nanoscale lead (II) bromide perovskites, that can have 2D, quasi-2D, or 3D layered structures, and may be prepared by relatively simple methods, including a one-pot synthesis procedure. The methods provided herein may be performed at room temperature, result in product yields of at least 70%, and/or produce metal halide perovskites of high quality. The nanoscale metal halide perovskites may be color tunable, be stable, and/or have high quantum efficiencies. The nanoscale metal halide perovskites provided herein may have different quantum size confinement to enable color tuning, and the quantum size confinement may be controlled by the methods provided herein.

In embodiments, the nanoscale metal halide perovskites provided herein comprise a crystal having a unit cell according to formula (I):

$$(RNH_3)(R'NH_3)(CH_3NH_3)_{n-1}M_nX_{3n+1} \quad (I);$$

wherein R and R' are selected independently from a monovalent $C_6$-$C_{20}$ hydrocarbyl; M is a metal selected from Pb, Sn, Cu, Ge, Mn, Co, Bi, or Eu; X is a halide ion selected from Cl, Br, or I; and n is an integer equal to or greater than 1. In one embodiment, n represents the number of inorganic metal halide layers.

In one embodiment of the nanoscale metal halide perovskites of formula (I), M is Pb, X is Br, and the nanoscale metal halide perovskites comprise a crystal having a unit cell according to formula (IA):

$$(RNH_3)(R'NH_3)(CH_3NH_3)_{n-1}Pb_nBr_{3n+1} \quad (IA).$$

In one embodiment of the nanoscale metal halide perovskites of formula (I), M is Pb, X is Br, R and R' are identical, and the nanoscale metal halide perovskite comprises a crystal having a unit cell according to formula (IB):

$$(RNH_3)_2(CH_3NH_3)_{n-1}Pb_nBr_{3n+1} \quad (IB).$$

In embodiments, the nanoscale metal halide perovskites provided herein comprise a crystal having a unit cell according to formula (II):

$$(RNH_3)(R'NH_3)(IC)_{n-1}M_nX_{3n+1} \quad (II);$$

wherein IC is an inorganic cation comprising a monovalent metal; R and R' are selected independently from a monovalent $C_6$-$C_{20}$ hydrocarbyl; M is a metal selected from Pb, Sn, Cu, Ge, Mn, Co, Bi, or Eu; X is a halide ion selected from Cl, Br, or I; and n is an integer equal to or greater than 1. In one embodiment, n represents the number of inorganic metal halide layers. In some embodiments, the monovalent metal comprises Cs or Rb. In a particular embodiment, the monovalent metal is Cs. In another embodiment, the monovalent metal is Rb.

In one embodiment of the nanoscale metal halide perovskites of formula (II), M is Pb, X is Br, and the nanoscale metal halide perovskites comprise a crystal having a unit cell according to formula (IIA):

$$(RNH_3)(R'NH_3)(IC)_{n-1}Pb_nBr_{3n+1} \quad (IIA).$$

In one embodiment of the nanoscale metal halide perovskites of formula (IIA), IC is Cs, and the nanoscale metal halide perovskites comprise a crystal having a unit cell according to formula (IIB):

$$(RNH_3)(R'NH_3)(Cs)_{n-1}Pb_nBr_{3n+1} \quad (IIB).$$

In one embodiment of the nanoscale metal halide perovskites of formula (II), IC is Cs, M is Pb, X is Br, R and R' are identical, and the nanoscale metal halide perovskite comprises a crystal having a unit cell according to formula (IIC):

$$(RNH_3)_2(Cs)_{n-1}Pb_nBr_{3n+1} \quad (IIC).$$

In the crystals having a unit cell according to any of formulas (I), (IA), (IB), (II), (IIA), (IIB), and (IIC), n may be [1] 1, thereby imparting the crystals with a 2D structure, [2] 2-9, thereby imparting the crystal with a quasi-2D structure, or [3] 10 or greater, thereby imparting the crystals with a 3D structure.

In one embodiment, R and R' are selected independently from a monovalent $C_7$-$C_{18}$ hydrocarbyl. In another embodiment, R and R' are selected independently from a monovalent $C_7$-$C_8$ hydrocarbyl. In yet another embodiment, R and R' are selected independently from a monovalent $C_{16}$-$C_{18}$ hydrocarbyl.

In one embodiment, R and R' are different monovalent $C_6$-$C_{20}$ hydrocarbyls. As used herein, the phrase "different monovalent $C_6$-$C_{20}$ hydrocarbyls" can refer to [1] two hydrocarbyls that include different numbers of carbon atoms; [2] two hydrocarbyls that include the same number of carbon atoms, but are substituted with the "—$NH_3$" functional groups at a different carbon atom; or [3] two hydrocarbyls that include the same number of carbon atoms, but are different stereoisomers. In another embodiment, R and R' are identical monovalent $C_6$-$C_{20}$ hydrocarbyls.

The phrases "$C_1$-$C_{20}$ hydrocarbyl," "$C_7$-$C_{18}$ hydrocarbyl," "$C_7$-$C_8$ hydrocarbyl," and the like, as used herein, generally refer to aliphatic, aryl, or arylalkyl groups containing 1 to 20, 7 to 18, or 7 to 8 carbon atoms, respectively. Examples of aliphatic groups, in each instance, include, but are not limited to, an alkyl group, a cycloalkyl group, an alkenyl group, a cycloalkenyl group, an alkynyl group, an alkadienyl group, a cyclic group, and the like, and includes all substituted, unsubstituted, branched, and linear analogs or derivatives thereof, in each instance having 1 to about 20 carbon atoms, 7 to 18 carbon atoms, 7 to 8 carbon atoms, etc. Examples of alkyl groups include, but are not limited to, methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl and dodecyl. Cycloalkyl moieties may be monocyclic or multicyclic, and examples include cyclopropyl, cyclobutyl, cyclopentyl, cyclohexyl, and adamantyl. Additional examples of alkyl moieties have linear, branched and/or cyclic portions (e.g., 1-ethyl-4-methyl-cyclohexyl). Representative alkenyl moieties include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl and 3-decenyl. Representative alkynyl moieties include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl and 9-decynyl. Examples of aryl or arylalkyl moieties include, but are not limited to, anthracenyl, azulenyl, biphenyl, fluorenyl, indan, indenyl, naphthyl, phenanthrenyl, phenyl, 1,2,3,4-tetra-hydro-naphthalene, tolyl, xylyl, mesityl, benzyl, and the like, including any heteroatom substituted derivative thereof.

Unless otherwise indicated, the term "substituted," when used to describe a chemical structure or moiety, refers to a derivative of that structure or moiety wherein one or more of its hydrogen atoms is substituted with a chemical moiety or functional group such as alcohol, alkoxy, alkanoyloxy, alkoxycarbonyl, alkenyl, alkyl (e.g., methyl, ethyl, propyl, t-butyl), alkynyl, alkylcarbonyloxy (—OC(O)alkyl), amide (—C(O)NH-alkyl- or -alkylNHC(O)alkyl), tertiary amine (such as alkylamino, arylamino, arylalkylamino), aryl, aryloxy, azo, carbamoyl (—NHC(O)O-alkyl- or —OC(O)NH-alkyl), carbamyl (e.g., $CONH_2$, as well as CONH-alkyl, CONH-aryl, and CONH-arylalkyl), carboxyl, carboxylic acid, cyano, ester, ether (e.g., methoxy, ethoxy), halo, haloalkyl (e.g., $—CCl_3$, $—CF_3$, $—C(CF_3)_3$), heteroalkyl, isocyanate, isothiocyanate, nitrile, nitro, phosphodiester, sulfide, sulfonamido (e.g., $SO_2NH_2$), sulfone, sulfonyl (including alkylsulfonyl, arylsulfonyl and arylalkylsulfonyl), sulfoxide, thiol (e.g., sulfhydryl, thioether) or urea (—NHCONH-alkyl-).

For example, R and R' may be selected independently from a monovalent $C_7$-$C_{18}$ hydrocarbyl that includes n-octadec-1-yl, n-oct-1-yl, or benzyl. In one embodiment, R is selected from a monovalent n-octadec-1-yl or a monovalent n-oct-1-yl, and R' is a monovalent benzyl. In another embodiment, R and R' are a monovalent n-octadec-1-yl. In a further embodiment, R and R' are a monovalent n-oct-1-yl. Therefore, in the crystals having a unit cell according to any of formulas (I), (IA), (IB), (II), (IIA), (IIB), and (IIC), [1] R and R' may be selected independently from a monovalent n-octadec-1-yl, a monovalent n-oct-1-yl, or a monovalent benzyl, [2] R may be selected from a monovalent n-octadec-1-yl or a monovalent n-oct-1-yl, and R' may be a monovalent benzyl, [3] R and R' may be a monovalent n-octadec-1-yl, and [4] R and R' may be a monovalent n-oct-1-yl.

Structures

The nanoscale metal halide perovskites provided herein generally may have a 2D structure, a quasi-2D structure, or a 3D structure.

Not wishing to be bound by any particular theory, it is believed that the value of "n" in unit cell formulas provided herein, such as "formula (I)" or "formula (II)," may determine whether a nanoscale metal halide perovskite has a 2D, quasi-2D, or 3D structure. As depicted schematically at FIG. 1, it is believed that at least in certain embodiments wherein M is Pb and X is Br, the nanoscale metal halide perovskites have a 2D structure when n is 1, a quasi-2D structure when n is 2 (see FIG. 1), 3 (see FIG. 1), or 4-9, and a 3D structure when n is 10 or greater.

As used herein, the phrases "2D structure" or "2D layered structure" generally refer to a crystal having unit cells of formula (I) or (II) wherein n is 1 (see FIG. 1), and, not wishing to be bound by any particular theory, it is believed that the crystals having a "2D structure" include a metal halide inorganic layer sandwiched between two organic layers.

As used herein, the phrases "3D structure" or "3D layered structure" generally refer to a crystal having unit cells of formula (I) or (II) wherein n is at least 10, for example, ∞ (see FIG. 1), and, not wishing to be bound by any particular theory, it is believed that the crystals having a "3D structure" include methylammonium metal halides capped with hydrocarbylamines.

As used herein, the phrases "quasi-2D structure" or "quasi-2D layered structure" generally refer to a crystal having unit cells of formula (I) or (II) wherein n is 2 (see FIG. 1), 3 (see FIG. 1), or 4-9, and, not wishing to be bound by any particular theory, it is believed that the crystals having a "quasi-2D structure" include "n" continuous metal halide layers sandwiched between two organic layers comprising hydrocarbylammonium ligations.

Not wishing to be bound by any particular theory, it is believed that synthetically manipulating a quasi-2D structure of a nanoscale metal halide perovskite can permit different quantum size confinement effects to be realized. The different quantum size confinement effects may enable precise color tuning of emission, for example, from deep blue to bright green. For example, the nanoscale metal halide perovskites depicted at FIG. 1 emit deep blue light when n is 1, blue light when n is 2, light blue light when n is 3, and bright green light when n is ∞.

In embodiments, the nanoscale metal halide perovskites provided herein emit light having a wavelength of about 403 nm (deep blue) to about 530 nm (bright green).

In embodiments, the nanoscale metal halide perovskites provided herein have a PLQE of about 13% to about 45%.

In embodiments, the the nanoscale metal halide perovskites provided herein emit light having a wavelength of about 403 nm (deep blue) to about 530 nm (bright green), and have a PLQE of about 13% to about 45%.

Methods for Making Nanoscale Perovskites

Methods also are provided for making nanoscale metal halide perovskites. The methods provided herein may permit synthetic control of "n" of the unit cell formulas herein. Not wishing to be bound by any particular theory, it is believed that controlling the value of "n" may result in different quantum size confinement in the nanoscale metal halide perovskites, thereby enabling color tuning. For example, it is believed, at least in certain embodiments, that increasing n of formula (I) or (II) herein from 1 to various integers and to infinity, the emission red-shifts from deep blue to bright green. This structure-property relationship may permit color tuning, because, at least in certain embodiments, the photophysical properties can correlate to the materials' composition and structure.

Alternatively or in addition to adjusting the n of formula (I) or (II) herein, it is believed that color tuning of the nanoscale metal halide perovskites provided herein can be realized, at least in some embodiments, by manipulating the organic cations. Not wishing to be bound by any particular theory, it is believed that manipulating the organic cations can afford 2D, quasi-2D, and/or 3D structures having different quantum confinement effects.

In embodiments, the methods comprise providing a precursor liquid comprising a first polar organic liquid, a metal halide, and at least two cations selected from the group consisting of [1] a small cation, [2] $RNH_3$, and [3] $R'NH_3$, wherein R and R' are selected independently from a monovalent $C_6$-$C_{20}$ hydrocarbyl, and the small cation is $CH_3NH_3$ or an inorganic cation comprising a monovalent metal; and contacting the precursor liquid with a second polar organic liquid to form the nanoscale metal halide perovskite. The ratio of the at least two cations may be manipulated. R and R' may be identical. In a particular embodiment, the at least two cations consist of $RNH_3$ and $R'NH_3$. The monovalent $C_6$-$C_{20}$ hydrocarbyl of R and R' may be independently selected from n-octadec-1-yl, n-oct-1-yl, or benzyl.

The metal halide may comprise Pb, Sn, Cu, Ge, Mn, Co, Bi, or Eu. In one embodiment, the metal halide is lead (II) halide. In a particular embodiment, the metal halide is lead (II) bromide.

The organic ammonium cations, i.e., $CH_3NH_3$, $RNH_3$, and $R'NH_3$, may be ammonium salts, such as $CH_3NH_3^-X^+$, $RNH_3^-X^+$, and $R'NH_3^-X^+$, wherein X is a halogen. In one embodiment, the at least two cations are ammonium salts prepared by adding a slight excess of HX, wherein X is a halogen, such as bromine, to an amine, such as $CH_3NH_2$, $RNH_2$, and $R'NH_2$. This addition may be performed at about 0° C. and/or in a $C_1$-$C_{10}$ alcohol, such as ethanol. The solvents then may be evaporated under vacuum. The amines may include octadecylamine, octylamine, benzylamine, methylamine, or a combination thereof. Not wishing to be bound by any particular theory, it is believed that nanoscale lead (II) bromide perovskites having a 2D structure may be prepared by using benzylamine as an amine; and amines having longer organic portions, such as octadecylammonium bromide, may be used to prepare nanoscale metal halide perovskites having a 3D structure.

The inorganic cation comprising a monovalent metal can be a monovalent metal halide, such as CsX or RbX, wherein X is a halogen, such as Br. In one embodiment, the monovalent metal halide is CsBr. In another embodiment, the monovalent metal halide is RbBr.

In embodiments, the methods comprise providing a first liquid comprising a metal halide and the first polar organic liquid; providing a second liquid comprising the at least two cations; and combining the first liquid and the second liquid to form the precursor liquid.

The precursor liquid may be transparent. In one embodiment, the precursor liquid comprises lead (II) bromide and is a transparent precursor liquid.

The first polar organic liquid of the precursor liquid generally may be any polar organic liquid that does not substantially impact the formation of the nanoscale metal halide perovkites. In one embodiment, the first polar organic liquid is dimethyl formamide (DMF).

In one embodiment, the methods further comprise contacting the precursor liquid with a non-polar organic liquid prior to contacting the precursor liquid with the second polar organic liquid. The non-polar liquid may comprise hexane, cyclohexane, isomers of hexane, or a combination thereof. In a particular embodiment, contacting the precursor liquid with the non-polar organic liquid, such as hexane, comprises injecting the precursor liquid into the non-polar liquid. The non-polar liquid, such as hexane, may be stirred before, during, and/or after the injection. The non-polar liquid also may be at room temperature before, during, and/or after the injection.

The methods may also comprise contacting the precursor liquid with a second polar organic liquid, such as acetone, to form the nanoscale metal halide perovskite. In one embodiment, contacting the precursor liquid with the second polar organic liquid, such as acetone, results in the formation of a colloidal liquid. The colloidal liquid may be centrifuged. The first and second polar liquids, the non-polar liquid, and/or any unreacted starting materials may be removed by any means known in the art.

The nanoscale metal halide perovskites may be produced at a yield of at least 50%, at least 65%, at least 70%, at least 75%, at least 80%, at least 85%, at least 90%, or at least 95%. The yield of nanoscale metal halide perovskites, unless otherwise noted, refers to the yield calculated from the results of thermogravimetric analysis, and is based on the weight of metal halide in the nanoscale perovskites compared to the weight of metal halide used in the reaction (starting amount). The as-prepared nanoscale metal halide perovskites can be re-dispersed in toluene.

EXAMPLES

The present invention is further illustrated by the following examples, which are not to be construed in any way as imposing limitations upon the scope thereof. On the contrary, it is to be clearly understood that resort may be had to various other aspects, embodiments, modifications, and equivalents thereof which, after reading the description herein, may suggest themselves to one of ordinary skill in the art without departing from the spirit of the present invention or the scope of the appended claims. Thus, other aspects of this invention will be apparent to those skilled in the art from consideration of the specification and practice of the invention disclosed herein.

Unless otherwise noted, the following materials were used in the following Examples. Lead (II) bromide (99.999%), methylamine solution (33 wt. % in absolute ethanol), octylamine (99%), benzylamine (99%), octadecylamine (99%) and hydrobromic acid (48%) were purchased from Sigma-Aldrich. Acetone (99.5%) was purchased from VWR. N,N-Dimethylformamide (99.9%), toluene (99.9%) and hexane (98.5%, mixture of isomers) were purchased from Sigma-Aldrich. All reagents and solvents were used without further purification unless otherwise stated. Spectroscopic grade solvents were used in the UV-Vis and photoluminescence spectroscopic measurements.

Example 1

Synthesis of Nanoscale Perovskites

A quasi-2D layered nanoperovskite was made by forming a first liquid by dissolving 0.1 mmol lead(II) bromide (0.10 mmol, 36.7 mg) in 200 μL DMF.

A second liquid was them formed by mixing 33.6 mg octylammonium bromide (0.16 mmol) and 11.2 mg methylammonium bromide (0.10 mmol) in 100 μL DMF.

The first liquid and the second liquid were them combined to form a clear precursor liquid (300 μL DMF in total), which was subsequently dropped into 2 mL hexanes with vigorously stirring for 5 min at room temperature.

The corresponding nanoperovskites were induced by adding 3 mL acetone, followed by centrifugation to remove the unreactive materials in the supernatant. This process afforded the final products at the yields shown at Table 1, which were calculated after drying the nanoperovskites under vacuum.

Using the foregoing procedure, a series of nanoscale perovskites were made with different organic ammonium bromides. The types and amounts of the organic ammonium bromides and amount of lead bromide used for each product are summarized at Table 1. The sample names, such as "NP403", indicate the maximum emission wavelength observed for each sample, i.e., 403 nm for "NP403".

TABLE 1

Composition of the nanoperovskites of
Example 1, according to TGA and $^1$H NMR.

| Product | Reagent | Starting amount/ mmol | Molar ratio [a] | Calculated ratio [b] | Chemical yield [c] |
|---|---|---|---|---|---|
| NP403 | $C_8H_{17}NH_3Br$ | 0.16 | 0.12 | 0.22 | 76% |
| | $C_6H_5CH_2NH_3Br$ | 0.24 | 1.82 | 1.78 | |
| | $PbBr_2$ | 0.10 | 1.00 | 1.00 | |
| NP442 | $C_8H_{17}NH_3Br$ | 0.20 | 1.46 | 0.67 | 74% |
| | $CH_3NH_3Br$ | 0.05 | 0.66 | 0.67 | |
| | $PbBr_2$ | 0.10 | 1.00 | 1.00 | |
| NP461 | $C_8H_{17}NH_3Br$ | 0.16 | 0.59 | 0.40 | 72% |
| | $CH_3NH_3Br$ | 0.10 | 0.81 | 0.80 | |
| | $PbBr_2$ | 0.10 | 1.00 | 1.00 | |
| NP499 | $C_8H_{17}NH_3Br$ | 0.07 | 0.11 | 0.18 | 75% |
| | $CH_3NH_3Br$ | 0.20 | 1.11 | 0.91 | |
| | $PbBr_2$ | 0.10 | 1.00 | 1.00 | |
| NP513 | $C_8H_{17}NH_3Br$ | 0.05 | 0.07 | 0.12 | 76% |
| | $CH_3NH_3Br$ | 0.20 | 1.12 | 0.94 | |
| | $PbBr_2$ | 0.10 | 1.00 | 1.00 | |
| NP530 | $C_{18}H_{37}NH_3Br$ | 0.01 | 0.04 | 0.06 | 75% |
| | $CH_3NH_3Br$ | 0.20 | 1.18 | 0.97 | |
| | $PbBr_2$ | 0.10 | 1.00 | 1.00 | |

[a] Calculated from the TGA and $^1$H NMR results, and based on the mol of $PbBr_2$;
[b] Calculated from the XRD and AFM results, and based on the chemical formula of $(RNH_3)_2(CH_3NH_3)_{n-1}Pb_nBr_{3n+1}$;
[c] Calculated from the TGA results, and based on the weight of $PbBr_2$ in the nanoperovskites compared to the weight of $PbBr_2$ used in the reaction (starting amount).

The molar ratios of the organic ligands in the samples of this Example were estimated by dissolving the samples in DMSO-$d_6$ and analyzing the $^1$H NMR spectra. The results are summarized at Table 1. The composition of the organic (ammonium bromides) and inorganic (lead bromide) moieties was also confirmed by TGA analysis. Two major weight losses were observed for all of the samples at 300° C. and 550° C., which was believed to correspond to the losses of the organic ammonium bromides and the inorganic lead bromides, respectively.

Based on the results from both NMR and TGA analysis, the molar ratio of each component in the samples was calculated (see Table 1). For NP442 and NP461, the molar ratios of methylammonium bromide to lead(II) bromide were 0.66 and 0.81, respectively, which were very close to the theoretical ratios of 2:3 and 4:5 in n=3 and n=5 quasi-2D layered structures. However, the calculated amount of octylammonium bromide was slightly larger than the theoretical value in both cases, which was believed to indicate that the aliphatic ammonium ligands acted not only as the building blocks of the perovskite structures, but also as surfactants to form and stabilize the reverse micelles in solutions.

To permit the relatively easy manipulation of the ratios of the organic cations, the ammonium salts were prepared first.

The organic ammonium bromide salts used to prepare the nanoperovskites of this example were prepared by adding a slight excess of a hydrobromic acid solution (48%) into the corresponding amines, respectively, in ethanol at 0° C. The ammonium salts were obtained after removal of the solvents and starting reagents under vacuum, followed by washing with ethyl ether by three times, after which the ammonium bromides were dried and kept in a desiccator for future use.

The as-prepared nanoperovskites of this Example were dispersed in toluene, and resulted in samples ranging from colorless to light green under ambient light. Under UV irradiation ($\lambda_{ex}$=365 nm), however, the nanoperovskites of this example exhibited a significant color change from deep blue to green. Not wishing to be bound by any particular theory, it was believed that this could be attributed to the quantum confinement caused by the quasi-2D layered structure having inorganic layers of different thicknesses.

Example 2

Characterization of Nanoscale Perovskites

To elucidate the composition and structure of the obtained lead(II) bromide nanoperovskites of Example 1, full characterizations with Transmission Electron Microscopy (TEM), X-Ray Diffraction (XRD), Atomic Force Microscopy (AFM), Proton Nuclear Magnetic Resonance (1H NMR), and Thermal Gravimetric Analysis (TGA) were carried out.

Nuclear Magnetic Resonance (1H-NMR):

1H NMR spectra were acquired at room temperature on Bruker AVANCE III NMR Spectrometers with a 500 MHz Bruker magnet. All chemical shifts (δ) were reported in ppm relative to tetramethylsilane (TMS).

Thermogravimetry Analysis (TGA):

TGA was carried out using a TA instruments Q50 TGA system. The samples were heated from room temperature (~22° C.) to 800° C. with at a rate of 5° C.·min$^{-1}$, under a nitrogen flux of 100 mL·min$^{-1}$.

X-Ray Powder Diffraction (XRPD):

The XRD analysis was performed on Panalytical X'PERT Pro Powder X-Ray Diffractometer using Copper X-ray tube (standard) radiation at a voltage of 40 kV and 40 mA, and X'Celerator RTMS detector. The diffraction pattern was scanned over the angular range of 5-70 degree (2θ) with a step size of 0.02, at room temperature.

Figure 3:
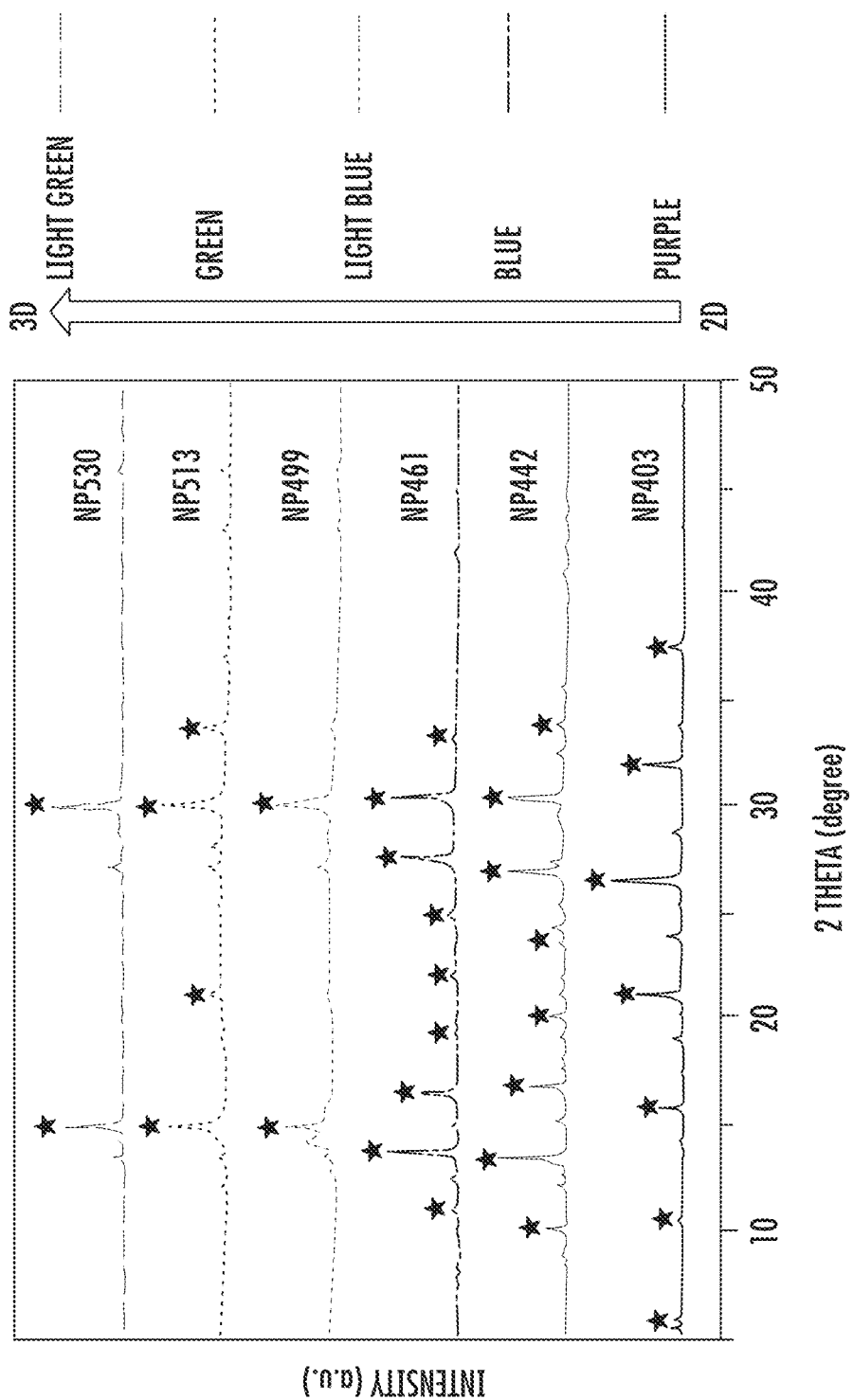
FIG. 3 depicts X-ray diffraction data for several embodiments of nanoscale metal halide perovskites.

The XRD patterns of the thin film samples of Example 1 were recorded as shown at FIG. 3 and summarized in Table 2, which can be used to quantify the layered crystalline structures of these NPs.

TABLE 2

XRD analyses including miller index,
2θ degree and lattice spaces (d).

| Sample | (h k l) | 2θ degree | d (Å) |
|---|---|---|---|
| NP403 | (0 0 2) | 5.29 | 16.67 |
| | (0 0 4) | 10.58 | 8.34 |
| | (0 0 6) | 15.93 | 5.54 |
| | (0 0 8) | 21.26 | 4.15 |
| | (0 0 10) | 26.66 | 3.31 |
| | (0 0 12) | 32.16 | 2.75 |
| | (0 0 14) | 37.66 | 2.35 |
| NP442 | (0 0 6) | 10.02 | 8.81 |
| | (0 0 8) | 13.36 | 6.61 |
| | (0 0 10) | 16.73 | 5.27 |
| | (0 0 12) | 20.13 | 4.39 |
| | (0 0 14) | 23.50 | 3.76 |
| | (0 0 16) | 26.93 | 3.28 |
| | (0 0 18) | 30.39 | 2.91 |
| | (0 0 20) | 33.85 | 2.61 |
| NP461 | (0 0 8) | 10.92 | 8.08 |
| | (0 0 10) | 13.68 | 6.45 |
| | (0 0 12) | 16.45 | 5.37 |
| | (0 0 14) | 19.22 | 4.59 |
| | (0 0 16) | 22.02 | 4.01 |
| | (0 0 18) | 24.87 | 3.55 |
| | (0 0 20) | 27.58 | 3.20 |
| | (0 0 22) | 30.42 | 2.90 |
| | (0 0 24) | 33.30 | 2.65 |
| NP499 | (0 0 1) | 14.88 | 5.93 |
| | (0 0 2) | 30.08 | 2.94 |
| NP513 | (0 0 1) | 14.88 | 5.93 |
| | (0 1 1) | 21.13 | 4.18 |
| | (0 0 2) | 30.07 | 2.94 |
| | (0 1 2) | 33.71 | 2.62 |

TABLE 2-continued

XRD analyses including miller index,
2θ degree and lattice spaces (d).

| Sample | (h k l) | 2θ degree | d (Å) |
|---|---|---|---|
| NP530 | (0 0 1) | 14.87 | 5.94 |
|  | (0 0 2) | 30.04 | 2.94 |

The (00l) diffraction peaks were observed in the NP403 thin film with layered spacing of 33.34 Å, which was believed to indicate the formation of benzylamine-based 2D perovskite products. This value was consistent with that of previously reported 2D perovskite nanomaterials.

Also, the layered spacing of NP442 was measured to be 52.86 Å, which was consistent with an n=3 quasi-2D layered perovskite structure in view of the fact that the interlayer spacing of octylamine-based 2D perovskites is 42.1 Å (42.1 Å+2×5.91 Å) (see N. Kitazawa et al. *Thin Solid Films*, 2006, 500, 133-137; and N. Kitazawa et al. *J Lumin*, 2009, 129, 1036-1041).

Figure 4:
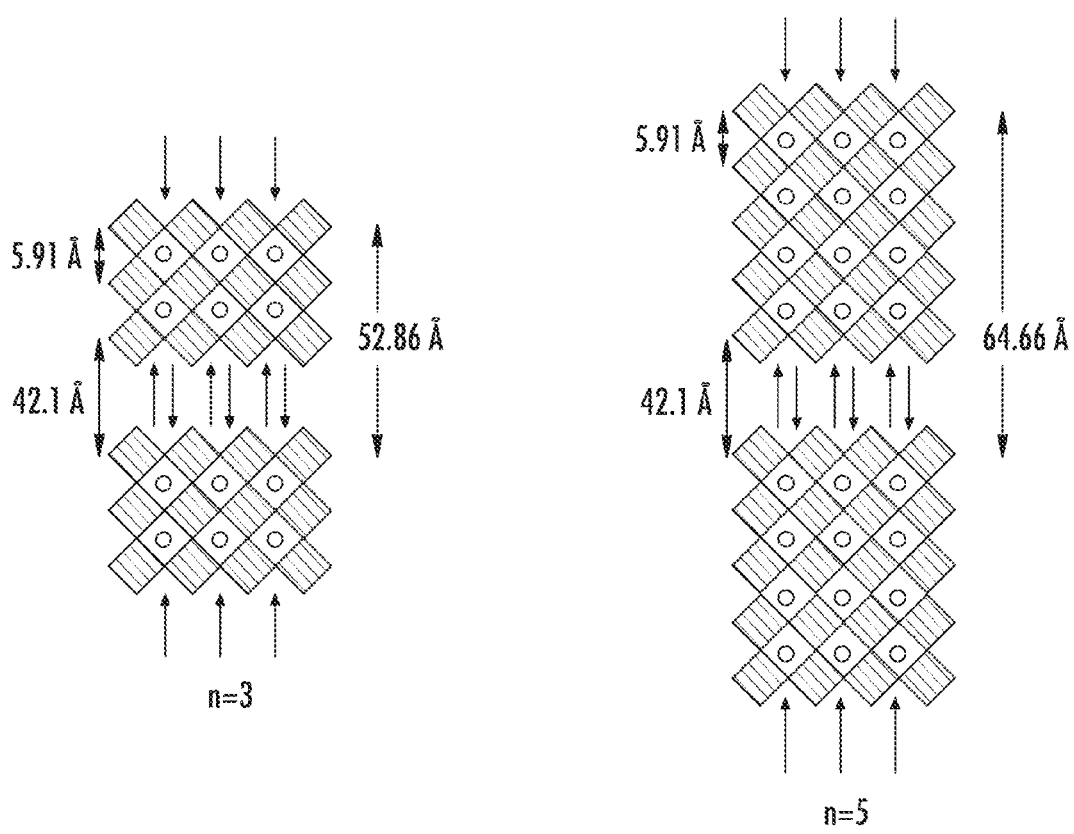
FIG. 4 depicts a schematic of various crystal structures of several embodiments having a quasi-2D structure.

The layered spacing of NP461 was measured to be 64.66 Å, which was equal to the layered spacing of NP442 plus two d-spacings of the cubic phase of 3D lead(II) bromide perovskites (52.86 Å+2×5.91 Å), which was believed to indicate that the n=5 quasi-2D layered perovskite structure was obtained. The large d-spacings calculated from the diffraction peaks of NP442 and NP461 were believed to confirm the formation of quasi-2D structure as shown at FIG. 4. When the number of inorganic layers increased further (i.e. NP499, NP513 and NP530), the (100) and (200) diffraction peaks from the 3D lead(II) bromide perovskite structures were observed. Not wishing to be bound by any particular theory, it was believed that the sets of the minor peaks (impurity) might have been introduced during the sample preparation of XRD spectra, probably due to the decomposition or aggregation of the samples.

Transmission Electron Microscopy Images (TEM):

Microstructural characterization was performed using TEM, on a JEOL JEM-ARM200 cF at 200 kV. Low intensity illumination and fast acquisition time were used during data collection to avoid beam damage. TEM samples were prepared by depositing a few drops of the perovskite solution on a carbon film supported copper grid (200 mesh); the samples were subsequently dried overnight.

Figure 5A:
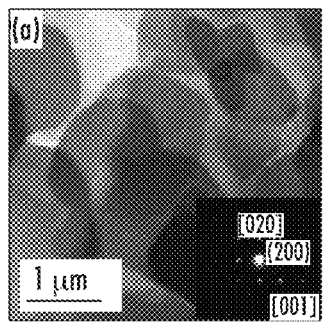
FIG. 5A is a transmission electron microscopy (TEM) image of one embodiment of a nanoscale metal halide perovskite and its electron diffraction pattern (inset).
Figure 5B:
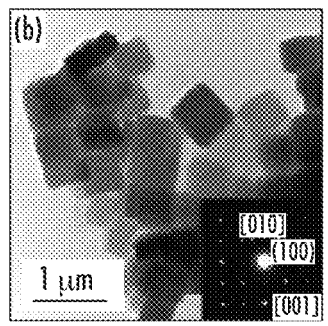
FIG. 5B is a TEM image of one embodiment of a nanoscale metal halide perovskite and its electron diffraction pattern (inset).
Figure 5C:
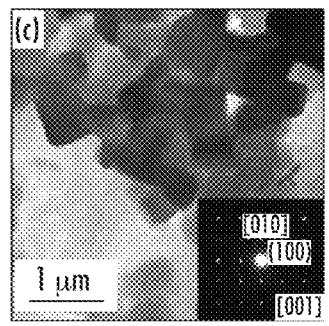
FIG. 5C is a TEM image of one embodiment of a nanoscale metal halide perovskite and its electron diffraction pattern (inset).
Figure 5D:
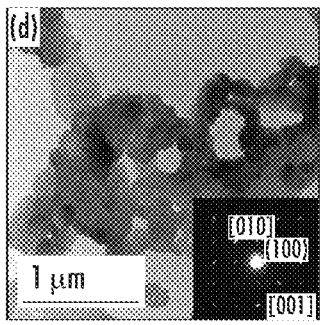
FIG. 5D is a TEM image of one embodiment of a nanoscale metal halide perovskite and its electron diffraction pattern (inset).
Figure 5E:
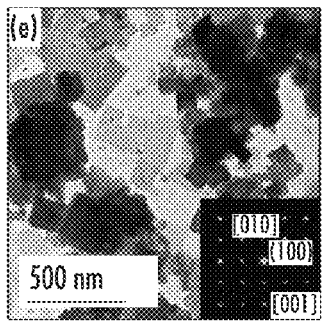
FIG. 5E is a TEM image of one embodiment of a nanoscale metal halide perovskite and its electron diffraction pattern (inset).
Figure 5F:
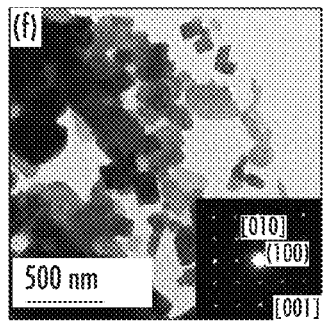
FIG. 5F is a TEM image of one embodiment of a nanoscale metal halide perovskite and its electron diffraction pattern (inset).

FIG. 5A, FIG. 5B, FIG. 5C, FIG. BD, FIG. 5E, and FIG. 5F are TEM images of NP403, NP442, NP461, NP499, NP513, and NP530, respectively, with their electron diffraction patterns (insets). All of the as-prepared metal halide perovskites displayed at least substantially rectangular single crystalline structures with a lateral dimension size of several hundred nanometers, except NP403, which had size dimensions on the order of several micrometers. The lateral size of the nanoscale metal halide perovskites decreased as the amount of methylammonium bromide increased, which was believed to suggest that the speed of the crystal growth in the lateral direction was faster than in the vertical direction for layered structures. The inserted electron diffraction patterns showed the [001] orientation diffraction patterns from the individual metal halide perovskites, which was believed to suggest a single crystalline structure for all the nanoscale metal halide perovskites. The d-spacing values measured from the electron diffraction patterns were 5.91±0.1 Å and 8.23±0.1 Å of the (100) plane, which corresponded to the cubic phases of the 3D perovskite $CH_3NH_3PbBr_3$ and tetragonal phases of the 2D perovskite $(C_6H_5CH_2NH_3)_2PbBr_4$, respectively.

Atomic Force Microscopy Images (AFM):

AFM measurements were conducted using Bruker Icon. All measurements were performed in the standard tapping mode with OTESPA-R3 tips from Bruker.

AFM was employed to further characterize the structure of the nanoscale metal halide perovskites of Example 1, in particular their thickness. Average thicknesses of 30-120 nm were observed for individual metal halide perovskites on a silicon wafer, which was believed to suggest that stacks of quasi-2D layered structures were obtained. The absence of the atomically thin perovskites was believed to rule out the thickness-dependent quantum confinement effect in this situation for the nanoscale metal halide perovskites.

Specifically, considering the fact that the thicknesses of a monolayer of NP403, NP442, and NP461 were 3.3 nm, 5.3 nm and 6.5 nm, respectively, from the XRD results, these three metal halide perovskites were found to contain approximately 9, 9, and 8 stacks of quasi-2D layered structures, respectively.

UV-Visible Measurements:

UV-Vis spectra were conducted at room temperature using a quartz spectrometer cuvette on a Varian Cary 100 Bio UV-Visible spectrophotometer.

Photoluminescence Steady State Studies:

Steady-state photoluminescence spectra were obtained at room temperature on a Varian Cary Eclipse Fluorescence spectrophotometer. All the data were acquired using a 1-cm semi-micro quartz cuvette. The emission spectra of the perovskites dispersed in toluene were measured under air atmosphere (unless otherwise indicated).

Photoluminescence Quantum Efficiencies:

For photoluminescence quantum efficiency measurement, the samples were excited at 360 nm. Absorbance at the excitation wavelength was kept below 0.1 to minimize the inner-filter effect. The fluorescence quantum yields were determined by comparing the integrated area of the corrected emission spectrum with that of the reference—quinine bisulfate ($\phi$=0.54 in 1 N $H_2SO_4$) (see, S. Fery-Forgues et al. *J. Chem. Ed.*, 1999, 76, 1260-1264).

Figure 2A:
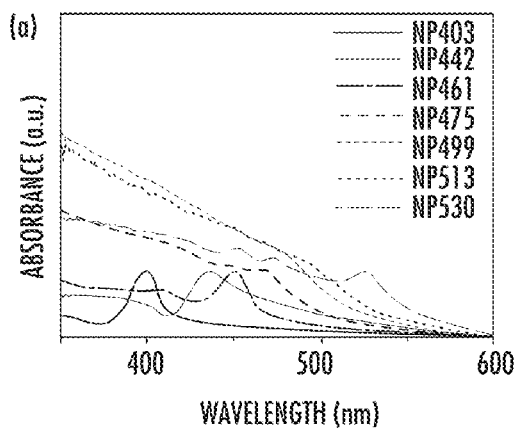
FIG. 2A depicts the absorbance spectra of several embodiments of nanoscale metal halide perovskites.
Figure 2B:
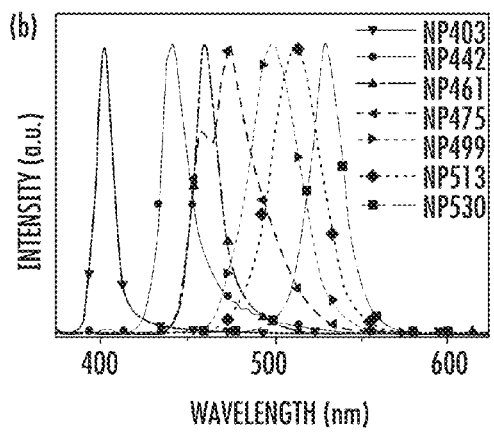
FIG. 2B depicts the emission intensity of several embodiments of nanoscale metal halide perovskites.

The absorption and emission of the nanoscale metal halide perovskites of Example 1 in toluene solutions were recorded, as shown at FIG. 2A and FIG. 2B, and summarized in Table 3. The absorption of the nanoscale metal halide perovskites was red shifted as the amount of methylammonium bromide used in the reaction was increased.

NP403 showed an absorption peak at 398 nm, which was consistent with previously reported 2D perovskites. For NP461 and NP442, it was believed that the main absorption peaks located at 451 nm and 437 nm, respectively, indicated the formation of quasi-2D layered perovskite products. Also, it was believed that the small, but discernible, peaks below the main peaks in both cases might have originated from an impurity (most likely the 2D structure). In the absorption spectrum of NP530, a peak at 525 nm was observed, which was identical to that of typical 3D lead(II) bromide perovskite nanomaterials reported previously. The absence of an obvious excitonic peak in NP499 and NP513 was believed to indicate a mixture of quasi-2D structures with different n values.

TABLE 3

Photophysical properties of the quasi-2D layered NPs.[a]

| Nanoperovskite | $\lambda_{abs}$ (nm) | $\lambda_{em}$ (nm) | FWHM (nm) | $\phi$ (%) |
|---|---|---|---|---|
| NP403 | 398 | 403 | 11 | 13.8% |
| NP442 | 437 | 442 | 16 | 24.5% |
| NP461 | 451 | 461 | 16 | 25.8% |

TABLE 3-continued

Photophysical properties of the quasi-2D layered NPs.[a]

| Nanoperovskite | $\lambda_{abs}$ (nm) | $\lambda_{em}$ (nm) | FWHM (nm) | φ (%) |
|---|---|---|---|---|
| NP499 | 490 | 499 | 34 | 44.3% |
| NP513 | 500 | 513 | 34 | 44.0% |
| NP530 | 525 | 530 | 21 | 20.2% |

[a]$\lambda_{abs}$ is the wavelength at absorbance maximum; $\lambda_{em}$ is the wavelength at emission maximum; φ is the photoluminescence quantum efficiency.

The photoluminescence spectra of as-prepared metal halide perovskites of Example 1 are shown at FIG. 2B. Ranging from 403 nm to 530 nm, the emissions had low full-width at half-maximum (FWHM) of 11-21 nm (except NP499 and NP513), which was believed to suggest that the products were of high purity. For sample NP475, a main peak at 475 nm appeared along with a small shoulder at 460 nm, which was believed to suggest a mixture of NP461 and NP475. The larger FWHMs of NP499 and NP513 (34 nm) also were believed to suggest the formation of a mixture of quasi-2D structures. The small Stokes shift of 5-13 nm in all of the samples was believed to imply that the photoluminescence of the nanoscale metal halide perovskites was generated from a direct exciton recombination process. All samples exhibited reasonably high PLQEs 13.8% (NP403) to 44.3% (NP499).

We claim:

1. A nanoscale metal halide perovskite crystal having a unit cell according to formula (I):

$$(RNH_3)(R'NH_3)(CH_3NH_3)_{n-1}MnX_{3n+1} \quad (I);$$

wherein R is $C_6$-$C_{20}$ hydrocarbyl;
R' is $C_6$-$C_{20}$ hydrocarbyl;
M is a metal selected from the group consisting of Pb, Sn, Cu, Ge, Mn, Co, Bi, and Eu;
X is a halide ion selected from the group consisting of Cl, Br, and I;
n is an integer equal to or greater than 1; and
R and R' are different when n is equal to 1.

2. The nanoscale metal halide perovskite of claim 1, wherein n is 1, and the crystal has a 2D structure.

3. The nanoscale metal halide perovskite of claim 1, wherein n is 2 to 9, and the crystal has a quasi-2D structure.

4. The nanoscale metal halide perovskite of claim 1, wherein n is an integer equal to or greater than 10, and the crystal has a 3D structure.

5. The nanoscale metal halide perovskite of claim 1, wherein R and R' are $C_7$-$C_{18}$ hydrocarbyl.

6. The nanoscale metal halide perovskite of claim 5, wherein R and R' are independently selected from the group consisting of n-octadec-1-yl, n-oct-1-yl, and benzyl.

7. The nanoscale metal halide perovskite of claim 1, wherein M is Pb, X is Br, n is 2 to 9, and the crystal has a quasi-2D structure.

8. The nanoscale metal halide perovskite of claim 1, wherein n is greater than 1, and R and R' are identical.

9. The nanoscale metal halide perovskite of claim 8, wherein R and R' are a monovalent n-oct-1-yl.

10. The nanoscale metal halide perovskite of claim 1, wherein the crystal emits light at a wavelength of 403 nm (deep blue) to 530 nm (bright green).

11. The nanoscale metal halide perovskite of claim 1, wherein the crystal has a PLQE of about 13% to about 45%.

* * * * *